(12) United States Patent
Philibin

(10) Patent No.: US 8,382,477 B2
(45) Date of Patent: Feb. 26, 2013

(54) HEALING ABUTMENT SYSTEM FOR BONE CONTOURING

(76) Inventor: Terry B. Philibin, Vienna, OH (US)

( * ) Notice: Subject to any disclaimer, the term of this patent is extended or adjusted under 35 U.S.C. 154(b) by 0 days.

(21) Appl. No.: 13/441,190

(22) Filed: Apr. 6, 2012

(65) Prior Publication Data

US 2012/0264081 A1 Oct. 18, 2012

Related U.S. Application Data

(60) Provisional application No. 61/476,360, filed on Apr. 18, 2011.

(51) Int. Cl.
*A61C 8/00* (2006.01)
(52) U.S. Cl. .................................................. 433/173
(58) Field of Classification Search .......... 433/173–176, 433/201.1
See application file for complete search history.

(56) References Cited

U.S. PATENT DOCUMENTS

| | | | |
|---|---|---|---|
| 4,431,416 A | 2/1984 | Niznick | |
| 4,488,875 A | 12/1984 | Niznick | |
| 4,645,453 A | 2/1987 | Niznick | |
| 4,758,161 A | 7/1988 | Niznick | |
| 4,781,591 A | 11/1988 | Allen | |
| 4,960,381 A | 10/1990 | Niznick | |
| 5,030,095 A | 7/1991 | Niznick | |
| 5,052,929 A * | 10/1991 | Seal | 433/173 |
| 5,061,181 A | 10/1991 | Niznick | |
| 5,062,800 A | 11/1991 | Niznick | |
| 5,071,350 A | 12/1991 | Niznick | |
| 5,076,788 A | 12/1991 | Niznick | |
| RE33,796 E | 1/1992 | Niznick | |
| 5,078,607 A | 1/1992 | Niznick | |
| 5,281,140 A | 1/1994 | Niznick | |
| 5,334,024 A | 8/1994 | Niznick | |
| 5,427,527 A | 6/1995 | Niznick et al. | |
| 5,433,606 A | 7/1995 | Niznick et al. | |
| 5,511,565 A | 4/1996 | Syers | |
| 5,571,017 A | 11/1996 | Niznick | |
| 5,575,650 A | 11/1996 | Niznick et al. | |
| 5,599,185 A | 2/1997 | Greenberg | |
| 5,622,500 A | 4/1997 | Niznick | |
| 5,636,989 A | 6/1997 | Somborac et al. | |
| 5,651,675 A | 7/1997 | Singer | |
| 5,674,069 A * | 10/1997 | Osorio | 433/172 |
| 5,759,034 A | 6/1998 | Daftary | |
| 5,782,636 A | 7/1998 | Armstrong et al. | |
| 5,871,358 A | 2/1999 | Ingber | |
| 5,885,079 A | 3/1999 | Niznick | |
| 5,899,697 A | 5/1999 | Lazzara | |
| 5,989,028 A | 11/1999 | Niznick | |
| 5,989,029 A * | 11/1999 | Osorio et al. | 433/173 |
| 6,120,293 A | 9/2000 | Lazzara | |
| 6,231,342 B1 * | 5/2001 | Osorio et al. | 433/173 |
| 6,244,867 B1 | 6/2001 | Aravena et al. | |
| 6,283,753 B1 | 9/2001 | Willoughby | |
| 6,287,117 B1 | 9/2001 | Niznick | |
| 6,368,108 B1 * | 4/2002 | Locante et al. | 433/173 |
| 6,386,876 B1 * | 5/2002 | Lee | 433/173 |
| 6,394,807 B2 | 5/2002 | Robinson | |

(Continued)

OTHER PUBLICATIONS

2011—Invibio Biomaterial Solutions.

(Continued)

*Primary Examiner* — Cris L Rodriguez
*Assistant Examiner* — Hao D Mai

(57) ABSTRACT

The present invention uses an anatomically shaped bone graft contouring abutment in place of a conventional healing abutment to control the bone graft for optimal height. The extraction site aesthetics, in the form of enhanced gingival growth, are facilitated by the optimal bone graft placement.

11 Claims, 6 Drawing Sheets

U.S. PATENT DOCUMENTS

| | | | |
|---|---|---|---|
| 6,537,070 | B1 | 3/2003 | Stucki-McCormick |
| 6,758,672 | B2 | 7/2004 | Porter |
| RE38,639 | E | 10/2004 | Oses et al. |
| 6,910,891 | B2 * | 6/2005 | Carroll .................... 433/173 |
| 7,014,464 | B2 | 3/2006 | Niznick |
| 7,108,510 | B2 | 9/2006 | Niznick |
| 7,264,469 | B2 | 9/2007 | Abarno |
| 7,341,453 | B2 | 3/2008 | Coatoam |
| 7,396,231 | B2 | 7/2008 | Niznick |
| 7,425,131 | B2 | 9/2008 | Amber |
| 7,677,891 | B2 | 3/2010 | Niznick |
| 7,699,613 | B2 | 4/2010 | Niznick |
| 7,708,557 | B2 | 5/2010 | Rubbert |
| 7,708,559 | B2 * | 5/2010 | Wohrle et al. ............. 433/174 |
| 7,785,107 | B2 | 8/2010 | Niznick |
| 2001/0021498 | A1 * | 9/2001 | Osorio et al. ............. 433/173 |
| 2005/0084821 | A1 * | 4/2005 | Sims et al. ............... 433/173 |
| 2006/0008773 | A1 | 1/2006 | Liao |
| 2007/0015110 | A1 * | 1/2007 | Zhang et al. ............. 433/173 |
| 2007/0020582 | A1 * | 1/2007 | Neumeyer ............... 433/173 |
| 2007/0065777 | A1 | 3/2007 | Becker |
| 2009/0047629 | A1 * | 2/2009 | Kim ....................... 433/173 |
| 2009/0280454 | A1 * | 11/2009 | Hanna ..................... 433/174 |
| 2010/0068674 | A1 * | 3/2010 | Zucker .................... 433/173 |
| 2010/0119995 | A1 * | 5/2010 | Grant et al. .............. 433/174 |
| 2010/0151421 | A1 * | 6/2010 | Devengencie et al. ..... 433/174 |
| 2010/0248187 | A1 * | 9/2010 | Naert et al. .............. 433/174 |
| 2010/0291507 | A1 * | 11/2010 | Abdelgany ............... 433/174 |
| 2012/0003610 | A1 * | 1/2012 | Llop ....................... 433/196 |

OTHER PUBLICATIONS

2006—Dental Implant Patient Handbook—American Assciation of Oral and Maxillofacial Surgeons.
Tarnow, et al.—The Effect of Inter-Implant Distance on the Height of Inter-Implant Bone Crest.
2005—Dental Implants—American Association of Oral and Maxillofacial Surgeons.
2007—Salama, et al.—Advantage of the Root Submergence Technique for Pontic Site Development in Esthetic Implant Therapy.
2003—Tarnow—Vertical Distance from the Crest of Bone to the Height of the Interproximal Papilla Between Adjacent Implants.
2001—Clinical and radiographic evaluation of the papilla level adjacent to single-tooth dental implants.
2005—Correlation of papilla to crestal bone levels around single tooth implants in immediate or delayed crown protocols.
2003—Journal of Practical Periodontics and Aesthetic Dentistry for the Anthology edition—The interproximal height of Bone . . . .
1992—Abstract—Journal of Periodontology—The Effect of the Distance from the Contact Point to the Credst of Bone on the.

* cited by examiner

HEALING ABUTMENT SYSTEM FOR BONE CONTOURING

PRIORITY INFORMATION

The present invention claims priority to U.S. Provisional Application No. 61/476,360 filed on Apr. 18, 2011, making reference herein to same in its entirety.

FIELD OF THE INVENTION

The present invention relates in general to implant dentistry. In particular, the present invention is directed to the maximization of interseptal alveolar bone height around a dental implant's most superior surface thereby optimizing final dental implant aesthetic results.

BACKGROUND ART

The success of implant dentistry was vastly improved by the incorporation of osseointegration. Osseointegration was originally discovered by Dr. P. Bränemark in the 1950s and 1960's using titanium implants. Dr. Branemark, an orthopedic surgeon, discovered that when titanium was implanted into bone, the two substances fused safely and securely. This appeared to provide a permanent solution to the old problem of replacing missing teeth with a durable, stable substitute for the original tooth.

However, what has been proven over time is that intimate bony contact with the dental implant is not the only condition for dental implant success. Bony anatomy at the superior aspect of the dental implant where it meets the eventual dental restoration or prosthesis is also very critical for dental implant success. Dental implant art continues to go through many modifications and evolutions in an attempt to maximize dental implant success, including aesthetic factors.

The result of more than a half century of development is a standardized set of implant hardware, and techniques for using that hardware. Dental implants and their accompanying extensions and abutments have a wide range of different shapes and designs. Examples are manufactured by Nobel Biocare, BioMet 3i, Strauman, Zimmer, BioHoizons, Implant Direct, and a number of others. Practitioners in this particular field are well aware of all the aforementioned hardware produced so that no additional elaboration is needed for an understanding of the background of this invention. Primers on implants are cited in the Information Disclosure Statements.

Historically, dental implants were placed in a surgical staged approach (two stages). The first surgical stage consisted of making an incision in the gingival tissue and reflecting the gingival tissue to the buccal and lingual to expose the alveolar bone. An osteotomy (hole to receive the dental implant fixture) would then be created in an increasing diameter stepwise fashion using a dental drill with low speed and high torque. The dental implant fixture (implant) would then be screwed or pressed into the osteotomy and the gingival tissue would be reapproximated and sutured closed.

After a healing period of two to six months, the second stage surgical procedure would be performed at which time a small flap or hole punch would be used to create a hole in the gingival tissue through which a healing collar (healing abutment) would be placed. The gingival tissue would then heal around the healing collar for two to four weeks, at which time the artificial tooth (crown) would be fabricated and placed by screwing or cementing it to the dental implant final abutment.

A key development in the implant art is the anti-rotational connection between the dental implant fixture embedded in the bone at the missing tooth or extraction site and the final abutment (which holds the prosthesis replacing the tooth) fixed to the implant fixture. The basic designs were developed by Niznick, and are disclosed in a plurality of patents originated by that individual. All of these patents are incorporated herein by reference, and cited in the Information Disclosure Statement.

The anti-rotational connection (for final or prosthetic abutments) patented by Niznick is so important in this art that it has become a key hardware standard, so that its absence in modern implant treatment for partially edentulous situations virtually never occurs. Furthermore, the use of these various anti-rotational connectors determine the techniques and procedures that have also become standard in modern implant dentistry. As such, further elaboration is not required.

Anti-rotational connections come in many shapes, including a hexagonal shape (by Zimmer and BioHorizons); a tri-lobed arrangement (Nobel Biocare); and, an octagon (Strauman), as well as a number of others on the market. By preventing rotation between the permanent (or final) abutment holding the crown complex (prosthesis) to the implant fixture, a high degree of stability is achieved.

Because of the reliability provided by such standard procedures and hardware, a great deal of modern implant dentistry can now be directed to aesthetics, and efficiency in conducting the overall replacement process (to prevent unnecessary discomfort to the patient). The overall process steps and armamentarium, from tooth extraction to placement of the final prosthesis at the edentulous site are crucial in that they determine the overall efficiency and pace of the surgical procedure (including patient discomfort), and most importantly the aesthetic characteristics of the final prosthesis and the surrounding anatomy.

More recent developments in the procedures by which dental implants are placed include performing both the first and second stage surgical procedures at one time (single stage implant surgery), and immediate placement of dental implants after tooth extraction. Single stage dental implant surgery can be described as placing the dental implant fixture and healing abutment or collar at the same time. The advantage of this is that the patient only has to go through one surgical procedure, thereby saving time and inconvenience for the patient.

Conventional healing collars were developed to better facilitate the second stage of the surgical process. This includes the insertion of the healing abutment into the implant through partially healed gingiva to guide the contouring of the gingiva. To facilitate this, conventional healing abutments have always been circular in cross section, and have always been rotatable to screw into the implant. This was done to create as little trauma as possible to the partially healed gingiva. The afore-mentioned anti-rotation locking devices would be unnecessary for conventional healing abutments due to the circular shape of the healing abutment and the need to easily slide them past partially healed gingiva to quickly and easily fit into an existing dental implant. In conventional implant dentistry, it is the permentant abutment supporting the crown or prosthesis, that requires the anti-rotational locking devices.

A disadvantage to the single stage surgical procedure is that maturation of the gingival tissue around a conventional circular cross-sectional (in the horizontal plane) healing collar, heals in a non-anatomic shape. This situation can make the placement of the final crown more difficult. As the gingival tissue matures in a non-anatomic shape it is less resilient to the outward pressure of the final crown's (prosthetic tooth) greater overall dimension and different shape, which can cause a mismatch between gingiva and crown. This can hinder the complete seating (cementation) of the final crown.

This situation can cause the crown to be incompletely connected onto the abutment, therefore requiring reduction of the crown's occlusal surface or resulting in open regions between the abutment and crown interface. Open regions between the abutment and crown can cause cement extrusion into the surgical site resulting in an inflammatory tissue response and compromised healing. Both stability and aesthetics can be compromised.

A disadvantage of immediate dental implant placement after tooth extraction is the possibility of initial reduced stability of the implant fixture due to the implant osteotomy not having the same shape as the tooth root socket. To address this, bone graft materials are often placed within the tooth root socket around the dental implant fixture to help bone completely form around the dental implant fixture. With lack of gingival tissue to help retain the bone graft, the graft can become unstable. A conventional circular healing abutment does not allow for complete occlusion of the gingival opening and stabilization of the bone graft.

Membranes made of different materials have been used in the past to attempt to stabilize bone graft materials. However, their lack of rigidity can also lead to bone graft instability. This lack of bone graft stability can lead to loss of the bone graft and non-ideal alveolar bone anatomy. Non-ideal alveolar bone anatomy around a dental implant will ultimately lead to displeasing aesthetic results.

In modern implant dentistry, the aesthetics of dental implants and the surrounding tissue have become paramount. The conventional art regarding healing abutments focuses largely on maintaining a gingival opening for the tooth restoration to traverse through. Conventional healing abutments have been designed with a circular cross sectional configuration so as to create a gingival opening to accept the restoration hardware (crown and holding abutment). Conventionally, there is a wide range of sizes and shapes available that create a circular cross sectional opening within the gingiva. Such systems have only occasionally been successful in contouring gingiva, and providing acceptable final aesthetic results.

Custom made temporary prostheses have also been used but are labor intensive, take multiple appointments, and do not contour, contain, and stabilize bone graft materials. These temporary prostheses are usually fabricated to gradually increase in size with the attempt to contour the gingival tissue over time. This approach can be very time consuming, expensive for the patient, and only addresses the gingival tissue.

History has shown that favorable final aesthetics is directly related to the shape of the gingival anatomy and shape of the interdental gingival papilla. Numerous studies (Tarnow, Salama, and the like) have shown that the final anatomic shape and appearance of the interdental papilla is directly affected by the height of the alveolar crestal bone and its distance from the interproximal contact point of the two adjacent tooth crowns. These studies are incorporated herein by reference.

It has been shown that the distance from the height of the alveolar crestal bone to the contact point can determine whether or not the interdental gingival papilla between the crowns will appear anatomically correct. If the distance between the two landmarks is less than the recommended guidelines, the practitioner can be relatively certain that the interdental papilla will fill the space between the tooth crowns leading to favorable aesthetics. If the distance between the landmarks is greater than the recommended guidelines then the probability for incomplete presence of the interdental papilla increases and esthetics becomes less favorable. However, conventional techniques have proven unreliable in controlling the desired contouring of gingiva.

Accordingly, there exists a need in implant dentistry for an enhanced healing abutment system for bone contouring, containment, and stabilization. An improved healing abutment would facilitate the desired bone shape and aesthetic result. The improved healing abutment system, whether stock or custom fabricated, would contour, contain, and stabilize bone graft material and ultimately facilitate formation of ideal alveolar crestal bone at a tooth extraction site. This creation of ideal alveolar bone anatomy would lead to ideal dental implant aesthetics.

SUMMARY INVENTION

It is a key object of the present invention to improve the aesthetic results of conventional implant dentistry.

It is still another object of the present invention to provide a healing abutment system that facilitates both surgical and restorative dental processes that are less uncomfortable, and less time consuming for the patent.

It is again an additional object of the present invention to provide a healing abutment system wherein prosthetic replacements for extracted teeth are accomplished more efficiently, and with improved aesthetic results, than with conventional systems.

It is an additional object of the present invention to use techniques similar to those conventionally used in order to obtain improvements in gingiva healing and aesthetic contouring over that found in the conventional art.

It is another object of the present invention to provide a key invention healing abutment system for bone contouring, containment, and stabilization.

It is a further object of the present invention to provide a healing abutment system for bone contouring, containment, and stabilization, which is more effective in contouring, containment, and stabilization of alveolar bone graft materials.

It is a further object of the present invention to provide a healing abutment system for bone contouring, containment, and stabilization in which the process and technique of placing healing abutments are made more effective in contouring, containment, and stabilization of alveolar bone graft materials.

It is an additional object of the present invention to provide a healing abutment system for bone contouring, containment, and stabilization in which the healing abutments are made more effective in contouring surrounding gingiva.

These and other goals and objects of the present invention are achieved by a healing abutment arranged to connect to a dental implant held in a jaw osteotomy at a site of an extracted tooth. The healing abutment includes a connection portion configured to connect to the dental implant. The healing abutment also includes a body portion configured to mimic at least partially the anatomy of the extracted tooth. The body portion includes a front surface, a rear surface and two side surfaces, wherein each of the side surfaces includes a concavity configured to collect and contour bone graft material.

Another embodiment of the present invention is directed to a method of contouring bone graft material around a dental implant held in an osteotomy at the site of an extracted tooth. The method includes placing bone graft material at the extraction site. Then, the bone graft material is contoured upwards and outwards with respect to the dental implant by tightening a bone graft contouring abutment to a top surface of the dental implant.

DETAILED DESCRIPTION OF THE PREFERRED EMBODIMENT

Figure 6:
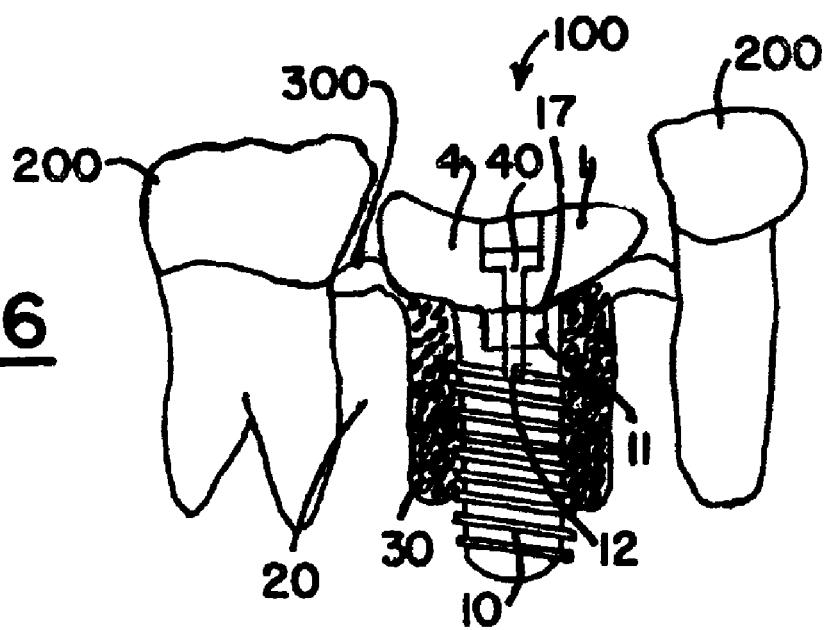
FIG. 6 is a front view of a dental implant site, in a jaw, between two existing teeth.
Figure 7:
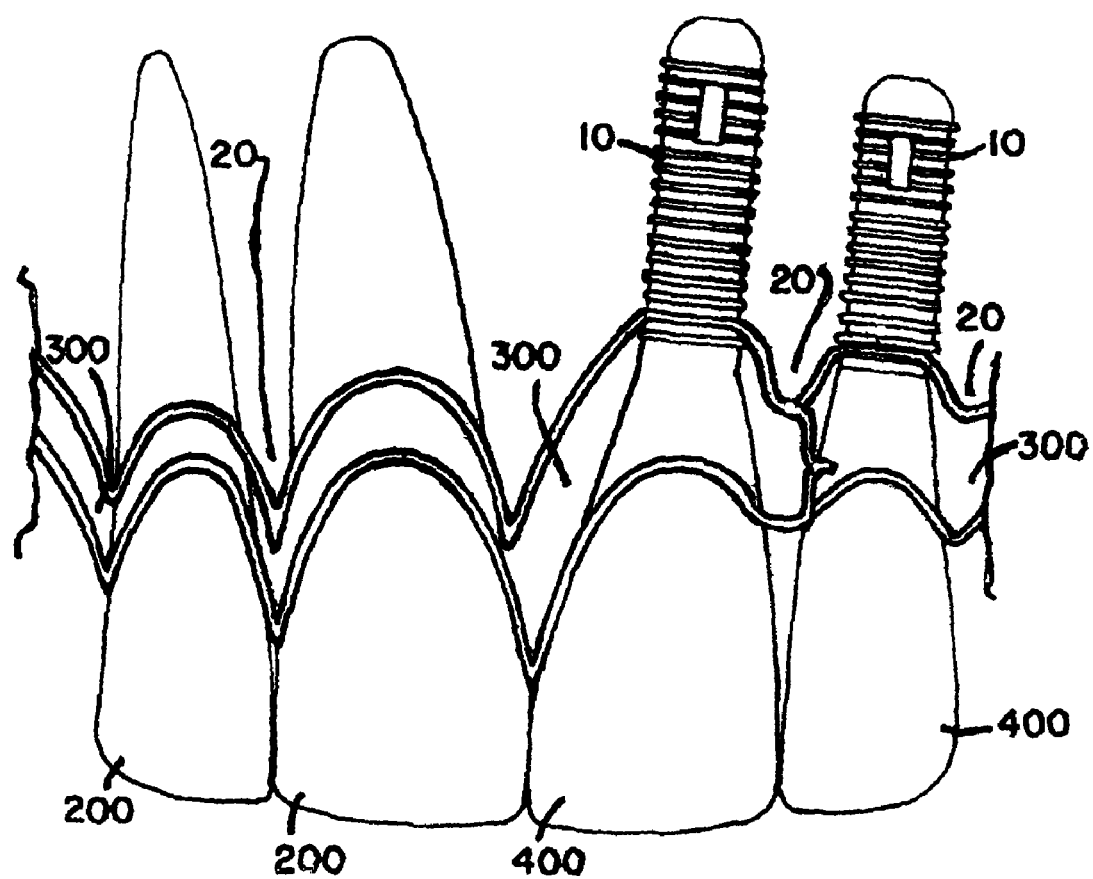
FIG. 7 is a front view of a jaw with dental implants having prosthetic devices, alongside natural teeth, illustrating key interseptal contact points.

The present invention is directed to a system for contouring bone growth at missing tooth or tooth extraction sites 100 (in FIG. 6). The environment hardware used is constituted by standard dental implants 10 as currently used in advanced implant dentistry. In the inventive system, at least a partially anatomic bone graft contouring abutment 1, as depicted in FIGS. 1-5, is attached to a standard implant 10, as depicted in FIGS. 6 and 7.

In the inventive system, the bone graft contouring abutment 1 is substituted for a conventional healing abutment. Bone graft material 30 is built up around bone graft contouring abutment 1 to help hold implant 10. Unlike conventional healing abutments, the bone graft contouring abutment of the present invention mimics at least partially, the anatomical characteristics of the extracted tooth/toothroot, at least in the horizontal plane. Accordingly, the size and shape of the bone graft contouring abutment 1 changes in accordance with the tooth that has been extracted, or was previously at the particular extraction site 100 (as depicted in FIG. 6).

Another difference in the bone graft contouring abutment 1 of the present invention is the use of an insert connection 2 having an anti-rotation locking configuration 21. In the present embodiment, this is a hexagonal arrangement with apices 211 that fit into a complementary through passage 11 in the dental implant 10, as depicted in FIG. 6. Anti-rotational locking mechanism 21 is important for the operation of the present invention in that it permits no lateral or rotational movement when the bone graft contouring abutment 1 is torqued (using threaded screw 40 in FIG. 6) onto the top of implant 10. This vertical torquing operation ensures the proper manipulation of the bone graft material 30 (as depicted in FIG. 6) that has been placed around the implant 10 and bone graft contouring abutment 1. The controlled-torque vertical movement of the bone graft contouring abutment 1, in conjunction with the structural aspects described infra, provides the desired functionality of the present inventive system.

The bone graft contouring abutment 1 appears to be similar to conventional healing abutments used for contouring gingiva. However, there are key distinctions. Besides the anti-rotational locking mechanism 21, an essential difference in the present invention is that the body portion 4 of the bone graft contouring abutment 1 mimics the anatomy of the tooth extracted from site 100. This mimicking is best found in the horizontal cross-section of the body portion 4. This cross-sectional shape changes along the length or height of the bone graft contouring abutment 1 in the same manner as it would along the extracted tooth.

The mimicking by the current bone graft contouring abutment 1 of the extracted tooth at site 100 is not limited to the horizontal cross-section at a single point. Rather, the mimicking can be done at multiple points along the height of the bone graft contouring abutment 1 of the present invention. Further, while the term "mimicking" can refer to an exact duplication of the horizontal cross-section of the extracted tooth by the bone graft contouring abutment 1 of the present invention, this mimicking need not mean an exact duplicate in size and shape. Rather, only a rough approximation of the general shape and size need be found in the bone graft contouring abutment 1 of the present invention. Accordingly, the definition of "mimic" can encompass anything from an exact duplicate of every aspect of the extracted tooth to a rough analogy of the extracted tooth by the general size and shape of the bone graft contouring abutment.

The key is that the shape of the bone graft contouring abutment 1 approximate that of the extracted tooth at site 100 so that the resulting bone growth can more effectively duplicate the size and shape (for aesthetic purposes) of the original jaw anatomy (interseptal alveolar bone) of the extraction site 100.

Along with the mimicking of the horizontal cross-sectional shape of the extracted tooth by corresponding parts of body portion 4, there are other novel structures in body portion 4 that facilitate the superior functionality of the present invention. In particular, the body portion 4 includes two side walls 41, a front wall 42 and a back wall 43. All have roughly convex shapes, curving outwards along the length of the body portion 4 as it extends from the mating surface 7 to the top or crown portion 46. The curvature of all four sides, in general, follows the curvature of the extracted tooth. However, side walls 41 also contain concavities 5 to gather, contain, contour and then stabilize the bone graft material (as depicted in FIG. 6).

Figure 1:
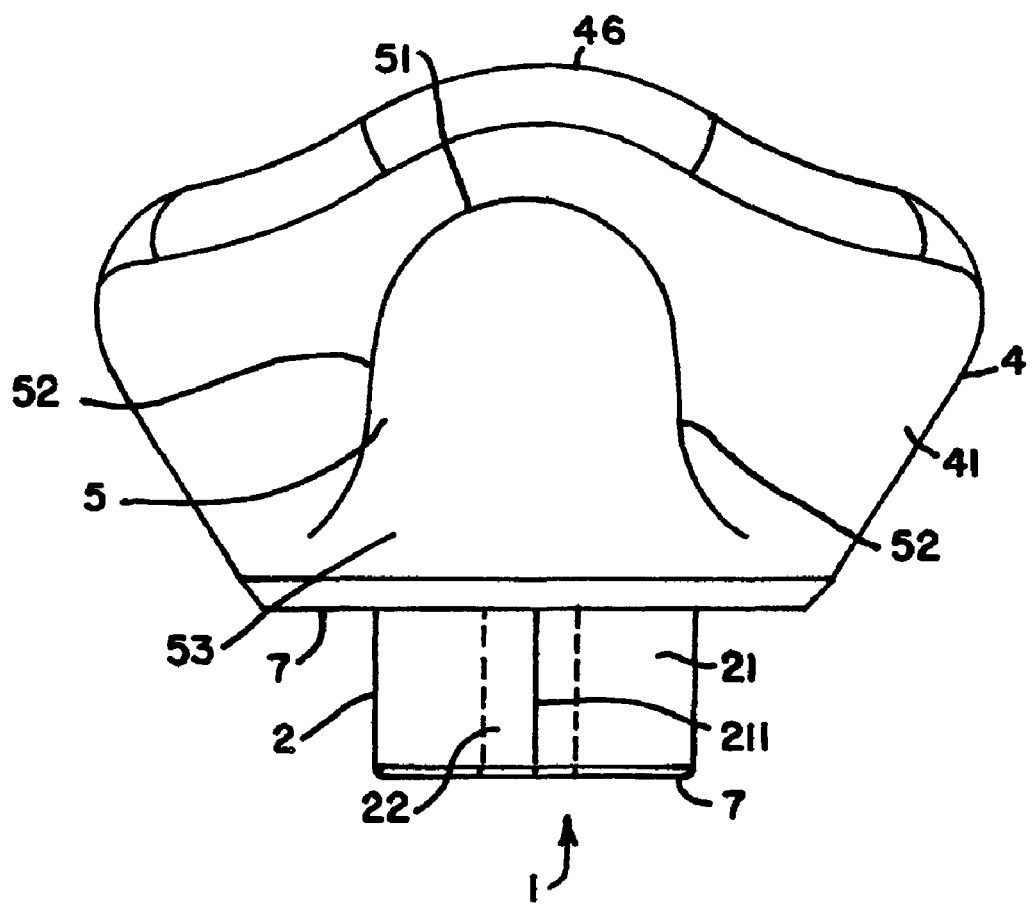
FIG. 1 is a side view of one example of a bone graft contouring abutment of the present invention.
Figure 2:
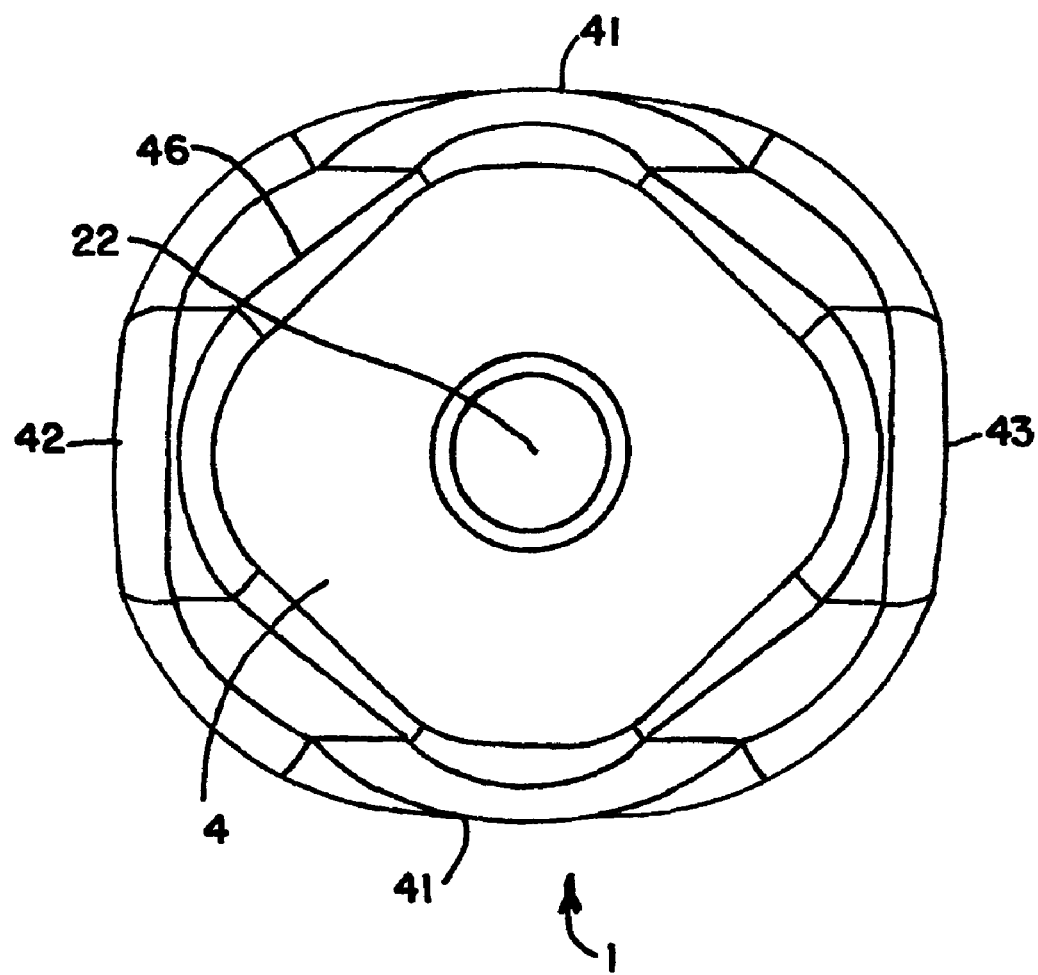
FIG. 2 is a top view of the bone graft contouring abutment from FIG. 1.

One example of concavity 5 is found in the side view constituted by FIG. 1. As depicted, the concavity 5 occupies approximately ⅓ of the side wall 41. However, the concavity 5 can occupy a smaller or larger proportion of side wall 41, depending upon the size and the shape of the overall bone graft contouring abutment 1, and the extracted tooth being mimicked. A key attribute is that concavities 5 be large enough to collect sufficient amounts of bone graft material 30 to fully stabilize the bone graft around implant 10 and to maximize the resulting interseptal (between the teeth) alveolar bone height. The maximizing of the final alveolar height is the purpose of mimicking the original alveolar bone 20 height around the extracted tooth at the subject extraction site 100. The final alveolar height can even be increased over that of the original to further enhance the aesthetic results.

Figure 3:
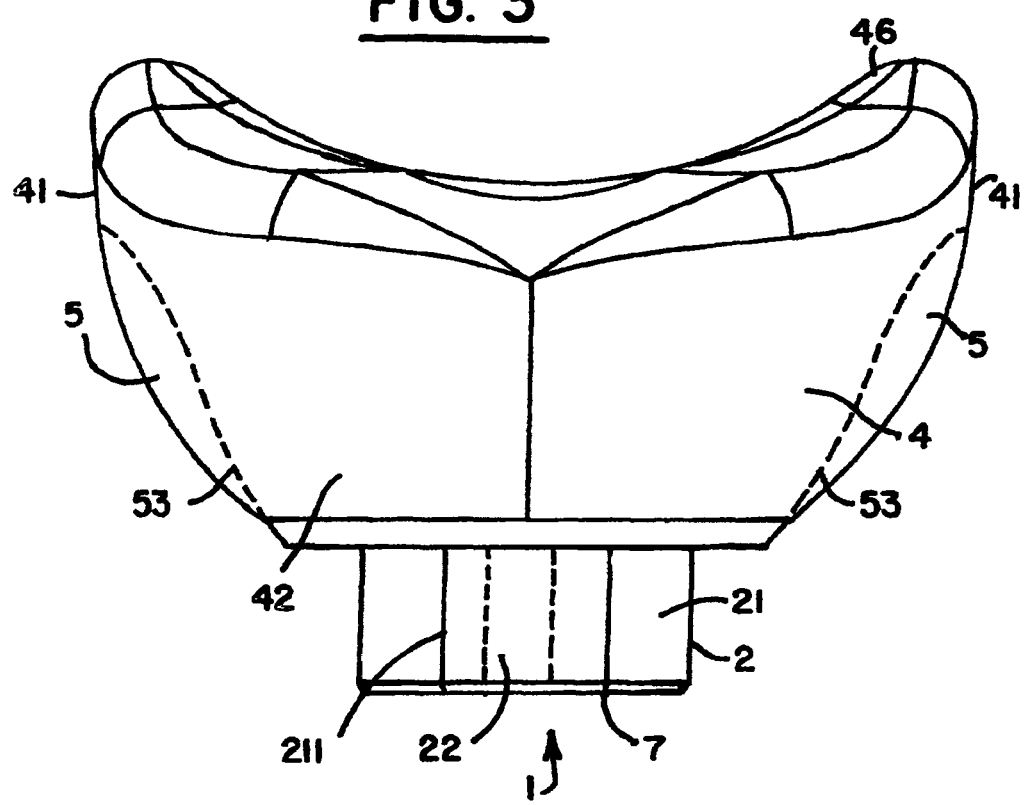
FIG. 3 is a front view (as seen looking into a patient's mouth) of the bone graft contouring abutment of FIGS. 1 and 2.

The convex side walls 41 with the upward curves (as depicted in FIG. 3), are modified by concavities 5 formed within side walls 41. The depth of the concavities 5 is minimal at the bottom near mating plate 7, and at a maximum, near the top periphery 51. Both the top periphery 51 and lateral peripheries 52 are formed by gently curing filets, constituting the interface between the concavities 5 and the convex side wall 41.

As depicted in the front view of FIG. 3, the deepest part of concavity 5 is near the upper periphery 51. This allows the maximum of bone graft material 30 to be accumulated in a position where it will be most easily forced into the desired positions (upwards and outwards from the bone graft contouring abutment 1) and the bone graft abutment 1 is torqued down onto the top of implant 10. The greatest depth with regard to the mesial-distal (front to back), as depicted in the side view of FIG. 1, is near the center midline of the body portion 4 of the bone graft contouring abutment 1. As a result, the depth of concavity 5 is somewhat less near lateral filets 52 than at the center of concavity 5.

Surface 53 near the bottom of concavity 5 has only a very slight slope so that the surface appears almost linear. This flat, shallow portion of concavity 5 facilitates movement of the bone graft material upwards towards the upper periphery 51. It aids in the accumulation of the bone graft material 30 near the periphery 51. From this position, the bone graft material 30 is forced upwards and outwards by the torquing of the bone graft contouring abutment 1 onto the top of dental implant 10.

Both upper periphery 51 and lateral peripheries 52 are formed by curved surfaces, or filets, in order to facilitate movement of the bone graft material 30 in desired directions. In particular, the bone graft material 30 must be moved upwards and outwards in order to maximize the height of the resulting interseptal (between teeth) bone structure. This, in turn, is crucial for the formation of aesthetically pleasing gingiva 300 growth between the prosthetic tooth 400 to be mounted on the implant 10, and adjacent teeth 200 (as depicted in FIG. 7).

The novel shape characteristics of the body portion 4 as well as the shape of the concavities 5, including depth, border shape, and location can change depending on the type and size of the extracted tooth and edentulous region. These shape characteristics can alter from tooth to tooth to provide maximized height of interseptal alveolar bone for any extraction site 100. The bone graft contouring abutment 1 is positioned and attached to dental implant 10 in a manner to contour, contain and stabilize the bone graft material 30 (in FIG. 4) in a desired manner for any extraction site 100 and for any type of tooth.

The alterations in the bone configuration (a combination of the existing alveolar bone 20 and the bone graft material 30, (as depicted in FIG. 6) will operate to contour the gingiva 50. By contouring the bone graft material 30 to maximize interseptal (between teeth) alveolar bone height and mimic the original buccal and lingual alveolar bone configuration and height, the gingiva 50 will be more precisely contoured than with conventional techniques in which the gingiva 50 is directly contoured.

It is also possible that the bone graft contouring abutment 1 will also operate to directly contour the gingiva 50 under some circumstances. However, this is not the primary function of bone graft contouring abutment 1. Rather, the shape of contouring abutment 1 is configured for bone graft contouring, containment, and stabilization rather than the direct contouring of gingiva. Contact with the contouring abutment 1 is primarily directed to bone graft material 30 (FIG. 6).

FIGS. 1-5 depict various views of one example of a bone graft contouring abutment 1 for one type of extracted tooth. Using the bone graft contouring abutment 1 as a substitute for a conventional healing abutment constitutes a key element of the present inventive system. The body portion 4 of bone graft contouring abutment 1 is selected to mimic the same horizontal cross sectional shape as the tooth/toothroot extracted from site 100. The concavities 5 on both sides 41 of body portion 4 act to contour, contain, and stabilize bone graft materials.

Figure 4:
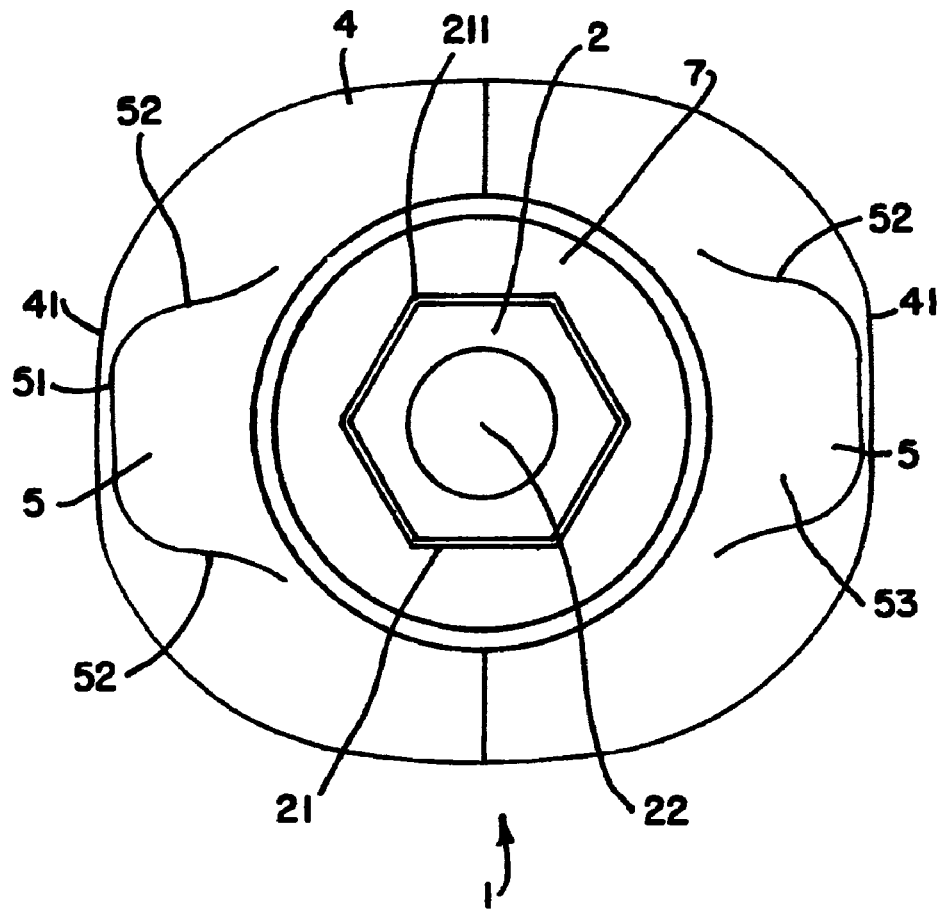
FIG. 4 is a bottom view of the bone graft contouring abutment of FIGS. 1-3, depicting the mechanical arrangement for connecting to an implant (not shown).
Figure 5:
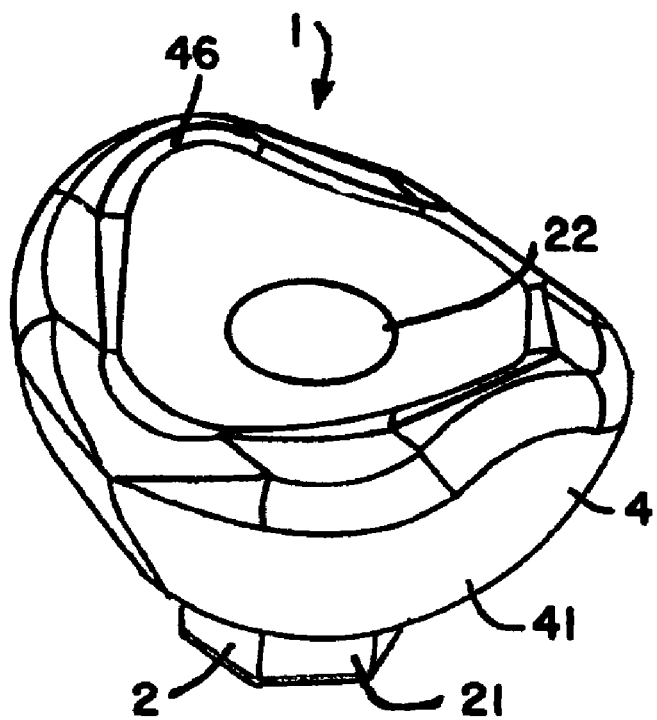
FIG. 5 is a front perspective view of the bone graft contouring abutment.

The bone graft contouring abutment 1 has a standard insert connection 2 which fits into a complementary through passage 11 of implant 10, which is located at extraction site 100 (as depicted in FIG. 6). Following conventional hardware standards, insert connection 2 has a standard anti-rotation locking mechanism 21 by virtue of a hexagonal shape (with apices 211), as depicted in FIG. 4. However, the anti-rotational locking mechanism 21 can be of any shape that facilitates anti-rotational locking. The hexagonal shape of connection insert section 2 is received in through passage 11 (in implant 10), which is also configured in a hexagonal shape. Accordingly, any rotation between implant 10 and the bone graft contouring abutment 1 is prevented. This anti-rotational locking connection 21 can be internal or external in arrangement, and can be of any shape or size conventional for dental implants.

It is important to note that the anti-rotational locking mechanism 21 used on the bone contouring healing abutment 1 of the present invention is not found in conventional healing abutments. Rather conventional healing abutments are of a one piece design and rotate easily into threaded portion 12 of the implant 10. The use of the anti-rotational locking mechanism 21 of the present invention helps facilitate the contouring, containment and stabilization of graft material through the tightening of the bone graft contouring abutment 1 to the dental implant 10 utilizing a screw fastener 40. Necessary tightening, and consequent contouring of the bone graft material 30, must take place without rotation of the abutment 1 so that there is no movement of the bone graft material 30. This arrangement leads to ideal healing and optimal interseptal alveolar bone 20 (in FIG. 6) height.

A close fit between the bone graft contouring abutment 1 and implant 10 is achieved by virtue of flat mating surfaces 7 (on bone graft contouring abutment 1) and 17 (constituting the top surface of implant 10). Both of the mating surfaces 7, 17 are machined smooth. The use of the two mating surfaces 7, 17 effects a tight fit, especially when screw 40 is torqued tight, holding the bone graft contouring abutment 1 to implant 10. The tight fit between mating surfaces 7, 17 make certain that no bone graft material 30 is able to migrate towards the implant 10, or be trapped between the implant 10 and the bone graft contouring abutment 1.

Continued tightening down of the abutment 1 to implant 10 compresses, contains, and stabilizes the bone graft material 30. The adjacent tooth 200 or adjacent bone graft contouring abutment 1 acts as lateral support for the bone graft material 30. In this way the interproximal bone height can be maximized. The near linear shape of surface 53 in concavity 5 of the bone graft contouring abutment acts to compress and stabilize the bone graft material 30 so as to reproduce ideal anatomic alveolar bone height between teeth, whether natural or prosthetic. This unique, three dimensional configuration of inventive abutment 1 ensures maximization of interseptal alveolar bone height, and resulting gingiva 300 aesthetics.

Conventionally, this would have been facilitated by simply attempting to spread bone graft material 30 along a conventional healing abutment in a painstaking manner, and hoping that bone graft material 30 would adhere. This would not have been possible with the smooth, truncated conical shape of conventional healing abutments, which are circular in the horizontal plane as well as linear in all vertical planes. This conventional component anatomy could not guide, contour, contain, and stabilize bone graft material 30 interproximately (between teeth) to produce increased interseptal bone (bone ridge between teeth) height.

The bone graft contouring abutment 1 contains a through passage 22, by which a screw fastener 40 passes to be received in a threaded portion 12 in implant 10. Fastener 40 is preferably threaded so that it can be used to apply pressure (via torque) to connect bone graft contouring abutment 1 to implant 10. This is done by applying the appropriate torque to fastener 40 in a normal manner. As previously stated, the effect of this is to force a sufficiency of bone graft material 30 both laterally outward and upward over the alveolar bone 20 on the mesial and distal aspects (along the entire depth from front to back) of the extraction site 100. This contouring of the bone graft material 30 results in a maximization of final interseptal alveolar bone height on which the gingiva 300 grows.

The contour of the combined bone 20 and bone graft material 30 creates the substrate on which the gingiva 300 will grow and rest on. The proper contour of alveolar bone 20 and bone graft material 30 results in the desired configuration of the gingiva 300 once the healing process is complete. Ideal gingival architecture and gingival interdental papilla anatomy directly correlates to favorable dental implant aesthetics.

Numerous studies (Tarnow, Salama, and the like) have shown that the final anatomic shape and appearance of the gingival interdental papilla 50 is directly affected by the height of the interseptal alveolar crestal bone (B in FIG. 7) as it relates to the interproximal contact point (A in FIG. 7) of the two adjacent tooth crowns (natural or artificial as depicted in FIG. 7). It has been shown that the distance from the height of the interseptal alveolar crestal bone (B) to the contact point (A) can determine whether or not the interdental papilla of gingival tissue 300 between the crowns will appear anatomically correct.

If the distance between the two points A and B is less than the recommended guidelines, the practitioner can be relatively certain that the gingival interdental papilla 300 will fill the space between the tooth crowns leading to favorable aesthetic results. If the distance between the landmarks is greater than the recommended guidelines then the probability for incomplete appearance of the gingival interdental papilla increases (black triangle syndrome), and the aesthetics becomes far less favorable.

In order to maximize the aesthetics (complete fill-in of the interdental papilla 300) the height of the interseptal alveolar crestal bone (B) (depicted in FIG. 7) is critical. The bone graft contouring abutment 1 of the present invention is used during immediate or delayed dental implant placement surgery to contour, contain, and stabilize bone grafting material in an ideal shape. The present inventive system is used to contour, contain, and stabilize bone graft material 30 in a manner to increase the interseptal alveolar crestal bone 20 height. The inventive bone graft contouring abutment 1 ideally shapes the bone substrate (both alveolar 20 and graft material 30) so as to maximize interseptal alveolar crestal bone height and mimic ideal alveolar crestal bone anatomy at all points around the extraction site 100.

The bone graft contouring abutment 1, of the present invention can be used during dental implant placement whether the dental implant is placed after tooth extraction (immediate placement), or after alveolar bone healing has taken place (delayed placement). When a dental implant 10 is placed at the time of tooth extraction there often exists at site 100 an extraction socket (osteotomy) substantially larger than the implant 1 in diameter. This open space would then be filled with a bone graft material 30 (autogenous, allogeneic, alloplastic growth factors/protein, as well as other graft materials). This bone graft material 30 would fill all voids within the tooth socket and may also be placed superior to the alveolar crest B (as depicted in FIG. 7) to increase the alveolar bone 20 height.

The bone graft contouring abutment 1, would then be connected to the dental implant and then, when tightened, the concavities 5 on both side walls 41 of the body portion 4 of the abutment 1 would guide, contour, contain, and stabilize the bone graft material 30. Bony healing requires stability of the graft material 30 in order for the bone graft to totally heal. The inventive bone graft contouring abutment 1, has the unique quality of holding bone grafting material 30 in the proper place as well as supporting the surrounding gingival soft tissue in the desired anatomic form.

While conventional healing abutments are made of high grade steels, this limitation is not necessary for the inventive bone graft contouring abutment 1. Rather, other materials have been found to facilitate the holding, contouring and stabilizing of bone graft material 30 better than the steel products used with the conventional healing abutments. One such example are the PEEK (poly ethyl ether ketone) materials developed and marketed by Invibio. These are thermoplastic bio-materials used in implantable medical devices. It has been found that such material exhibits excellent soft tissue compatibility. Further, this is a material that is more easily shaped for the particular details required by the present inventive bone graft contouring abutment 1. This material can be worked by injection molding, machining or other appropriate techniques.

Additional information on Invibio PEEK products are found in the attached IDS (Information Disclosure Statement) and are incorporated herein by reference.

When placement of a dental implant 10 is delayed (two stepped process), often the alveolar bone 20 is irregular in shape and may not provide the ideal alveolar crestal bone height. Bone grafting can also be performed at this time so as to recreate an ideal alveolar shape thereby maximizing the interseptal alveolar crest bone height. Here, once again, the bone graft contouring abutment 1 can be placed so as to contour, contain, and stabilize the bone graft material 30 thereby optimizing alveolar shape as well as maximizing the resulting interseptal alveolar crestal bone height.

The technique of the present bone graft contouring system (using bone graft contouring abutment 1) begins with the ideal placement of a dental implant 10. A presurgical diagnostic workup is performed and conventional surgical placement guides are utilized. These guides may be based on traditional plain film x-rays, three dimensional cone beam ct data, or digital scanning methods. The surgical guides may be handmade, milled, or printed utilizing traditional methodology or computer aided machining techniques. The surgical guide is utilized to assist in the ideal dental implant placement. Ideal placement encompasses proper location in the x, y, and z, axis along with proper trajectory of the implant 10 as well as proper depth. Traditionally the proper location of the bone level implant platform 10 is 3-5 mm apical to the adjacent teeth's cemento-enamel junctions (as depicted in FIG. 7).

Following placement of the implant 10, bone grafting material 30 (autogenous, allogeneic, alloplastic, any other) is placed in any voids around the implant and compressed fully. The graft is also placed around the crestal alveolous so as to optimize alveolar anatomy and increase interseptal bone height.

The bone graft contouring abutment 1 is then placed on the implant 10 and is attached to the implant. The retainment screw 40 is then placed and tightened to the desired torque. This forces the bone graft contouring abutment 1 into place thereby contouring, containing, and stabilizing the bone graft material 30 in an ideal non-mobile rigid fashion. The tightening of screw 40 forces bone graft material 30 outward (laterally) and upward. The bone graft contouring abutment 1 is left in place until osseointegration of the dental implant 10 is complete (usually less than six months). The bone graft contouring abutment 1 can then be removed to reveal ideal alveolar bone anatomy, maximized interseptal bone height, and an ideal emergence profile of the gingival tissue. Restorative dental procedures (formation and placement of prosthetic restorations) can then be initiated.

While a number of embodiments for both hardware and implant procedures have been described by way of example, the present invention is not limited thereto. Rather, the present inventive system should be understood to include any and all variations, permutations, evolutions, derivations, adaptations and other embodiments that would occur to one skilled in this art, having possession of the present inventive teachings. Accordingly, the present invention should be limited only by the following claims.

I claim:

1. A bone graft contouring abutment to connect to a dental implant held in a jaw osteotomy at a site of an extracted tooth, said bone graft contouring abutment comprising:
   a) a connection portion being shaped to closely mate with said dental implant; and,
   b) a body portion having a longitudinal height extending upwards from said connection portion, and at least partially shaped along its longitudinal height to the anatomy of said extracted tooth, said body portion including a front surface, a rear surface and two convex side surfaces increasing in width along said longitudinal height, wherein each said convex side surface comprises a concavity formed within said convex side surface and having a depth substantially perpendicular to an axis of said longitudinal height, each said concavity extending along a substantial portion of said body longitudinal height, and increasing in depth as said longitudinal height of said body increases to collect and contour bone graft material.

2. The bone graft contouring abutment of claim 1, wherein said connection portion comprises an anti-rotational locking device.

3. The bone graft contouring abutment of claim 2, wherein said connection portion further comprises a mating plate configured to interface with a complementary mating plate on said dental implant.

4. The bone graft contouring abutment of claim 3, further comprising a through passage configured to align with an aperture on said dental implant, and accommodate a torquing device to pass therethrough and connect to said dental implant.

5. The bone graft contouring abutment of claim 1, comprising poly ethyl ether ketone.

6. The bone graft contouring abutment of claim 1, wherein a horizontal cross section for at least one point along a length of said body portion mimics a horizontal cross section of said extracted tooth at least one point along a length of said extracted tooth.

7. The bone graft contouring abutment of claim 1, wherein said concavities each comprise an upper lip and two lateral lips.

8. The bone graft contouring abutment of claim 7, wherein said upper and lateral lips of each said concavity comprise curved surfaces connecting each said concavity to a surrounding convex side surface.

9. The bone graft contouring abutment of claim 8, wherein said concavity comprises a substantially flat angled surface between said lateral lips at a bottom portion of said concavity.

10. The bone graft contouring abutment of claim 9, wherein said concavity is deeper near a center of said concavity than at said lateral lips.

11. The bone graft contouring abutment of claim 10, wherein said concavity defines a curvature configured to facilitate collection of bone graft material near said top lip.

* * * * *